United States Patent [19]

Rearden

[11] Patent Number: 5,552,529

[45] Date of Patent: Sep. 3, 1996

[54] AUTOANTIGEN, PINCH

[75] Inventor: Ann Rearden, Rancho Santa Fe, Calif.

[73] Assignee: The Regents of the University of California, Oakland, Calif.

[21] Appl. No.: 269,441

[22] Filed: Jun. 30, 1994

[51] Int. Cl.$^6$ .............................. C07K 14/47; C07K 7/06
[52] U.S. Cl. ....................... 530/380; 530/327; 530/806; 530/829; 424/185.1
[58] Field of Search .................................... 530/300, 327, 530/350, 380, 295, 806, 829; 424/185.1

Primary Examiner—Thomas M. Cunningham
Attorney, Agent, or Firm—Fish & Richardson, P.C.

[57] ABSTRACT

A novel autoantigenic polypeptide, PINCH, polynucleotides and antibodies that bind to PINCH are provided. A method for removing autoantibodies that bind to an epitope contained in PINCH from a sample, such as blood, and a method of treating autoimmune disorders associated with autoantibodies that bind an epitope in PINCH are also provided.

2 Claims, 6 Drawing Sheets

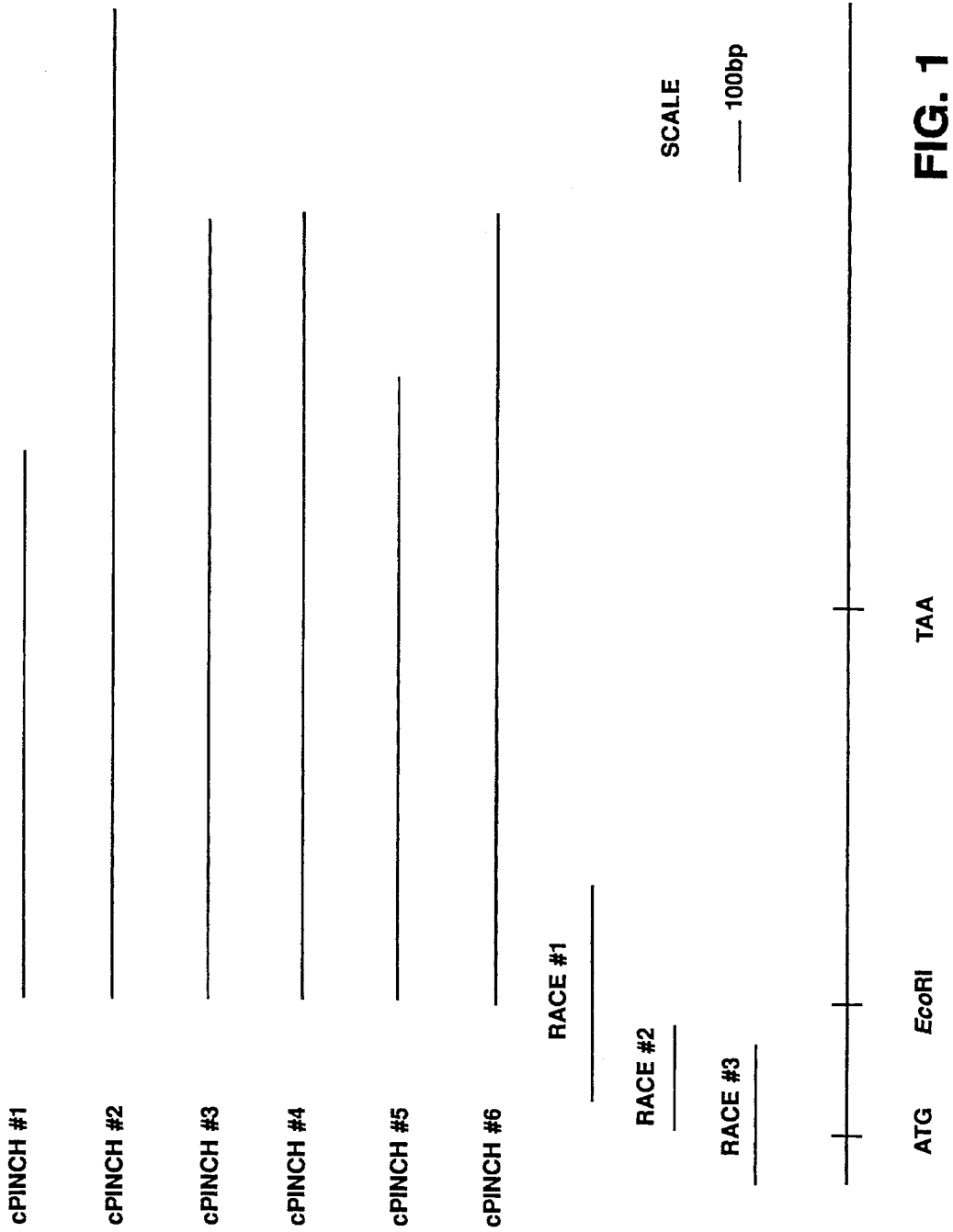

```
ATG GCC AAC GCC CTG GCC AGC GCC ACT TGC GAG CGC TGC AAG GGC GGC TTT GCG CCC GCT  60
Met Ala Asn Ala Leu Ala Ser Ala Thr Cys Glu Arg Cys Lys Gly Gly Phe Ala Pro Ala

GAG AAG ATC GTG AAC AGT AAT GGG GAG CTG TAC CAT GAG CAG TGT TTC GTG TGC GCT CAG  120
Glu Lys Ile Val Asn Ser Asn Gly Glu Leu Tyr His Glu Gln Cys Phe Val Cys Ala Gln

TGC TTC CAG CAG TTC CCA GAA GGA CTC TTC TAT GAG TTT GAA GGA AGA AAG TAC TGT GAA  180
Cys Phe Gln Gln Phe Pro Glu Gly Leu Phe Tyr Glu Phe Glu Gly Arg Lys Tyr Cys Glu

CAT GAC TTT CAG ATG CTC TTT GCC CCT TGC TGT CAT CAG TGT GGT GAA TTC ATC ATT GGC  240
His Asp Phe Gln Met Leu Phe Ala Pro Cys Cys His Gln Cys Gly Glu Phe Ile Ile Gly

♦                                                    300
CGA GTT ATC AAA GCC ATG AAT AAC AGC TGG CAT CCG GAG TGC TTC CGC TGT GAC CTC TGC
Arg Val Ile Lys Ala Met Asn Asn Ser Trp His Pro Glu Cys Phe Arg Cys Asp Leu Cys

********360
CAG GAA GTT CTG GCA GAT ATC GGG TTT GTC AAG AAT GCT GGG AGA CAC CTG TGT CGC CCC
Gln Glu Val Leu Ala Asp Ile Gly Phe Val Lys Asn Ala Gly Arg His Leu Cys Arg Pro

*******                                          ****************** 420
TGT CAT AAT CGT GAG AAA GCC AGA GGC CTT GGG AAA TAC ATC TGC CAG AAA TGC CAT GCT
Cys His Asn Arg Glu Lys Ala Arg Gly Leu Gly Lys Tyr Ile Cys Gln Lys Cys His Ala

---------------------------------- 480
ATC ATC GAT GAG CAG CCT CTG ATA TTC AAG AAC GAC CCC TAC CAT CCA GAC CAT TTC AAC
Ile Ile Asp Glu Gln Pro Leu Ile Phe Lys Asn Asp Pro Tyr His Pro Asp His Phe Asn

540
TGC GCC AAC TGC GGG AAG GAG CTG ACT GCC GAT GCA CGG GAG CTG AAA GGG GAG CTA TAC
Cys Ala Asn Cys Gly Lys Glu Leu Thr Ala Asp Ala Arg Glu Leu Lys Gly Glu Leu Tyr

********************                                                 600
TGC CTC CCA TGC CAT GAT AAA ATG GGG GTC CCC ATC TGT GGT GCT TGC CGA CGG CCC ATC
Cys Leu Pro Cys His Asp Lys Met Gly Val Pro Ile Cys Gly Ala Cys Arg Arg Pro Ile

660
GAA GGG CGC GTG GTG AAC GCT ATG GGC AAG CAG TGG CAT GTG GAG CAT TTT GTT TGT GCC
Glu Gly Arg Val Val Asn Ala Met Gly Lys Gln Trp His Val Glu His Phe Val Cys Ala

720
AAG TGT GAG AAA CCC TTT CTT GGA CAT CGC CAT TAT GAG AGG AAA GGC CTG GCA TAT TGT
Lys Cys Glu Lys Pro Phe Leu Gly His Arg His Tyr Glu Arg Lys Gly Leu Ala Tyr Cys

780
GAA ACT CAC TAT AAC CAG CTA TTT GGT GAT GTT TGC TTC CAC TGC AAT CGT GTT ATA GAA
Glu Thr His Tyr Asn Gln Leu Phe Gly Asp Val Cys Phe His Cys Asn Arg Val Ile Glu

840
GGT GAT GTG GTC TCT GCT CTT AAT AAG GCC TGG TGC GTG AAC TGC TTT GCC TGT TCT ACC
Gly Asp Val Val Ser Ala Leu Asn Lys Ala Trp Cys Val Asn Cys Phe Ala Cys Ser Thr

900
TGC AAC ACT AAA TTA ACA CTC AAG AAT AAG TTT GTG GAG TTT GAC ATG AAG CCA GTC TGT
Cys Asn Thr Lys Leu Thr Leu Lys Asn Lys Phe Val Glu Phe Asp Met Lys Pro Val Cys

AAG AAG TGC TAT GAG ATT TCC ATT GGA GCT GAA GAA AAG ACT
Lys Lys Cys Tyr Glu Ile Ser Ile Gly Ala Glu Glu Lys Thr
```

FIG. 2

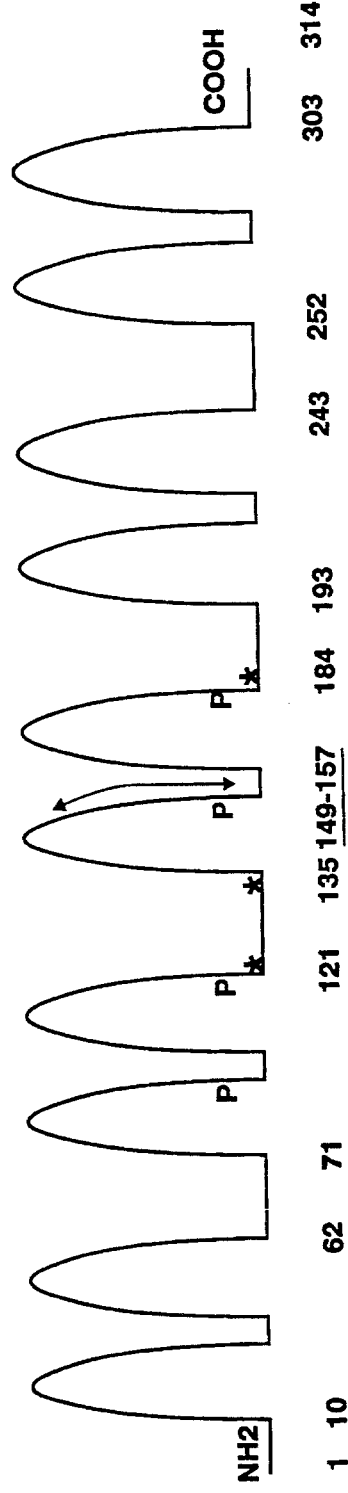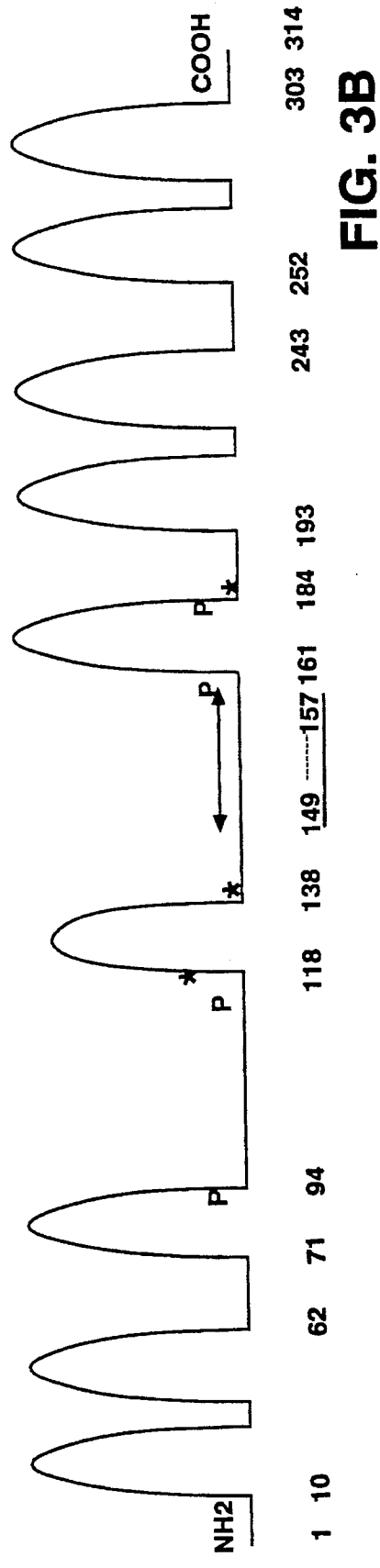

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 1246 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: PINCH ( i x ) FEATURE:
    ( A ) NAME/KEY: CDS
    ( B ) LOCATION: 120..1061

( x i ) SEQUENCE DESCRIPTION: SEQ ID NO:1:

```
TAGTTCAAGA CAACAGAGAC AAAGCTAAGA TGAGGAAGTT CTGTACAGTT TAGGAAATAG      60

AGGCTTTCAA AGATAATTCG CAGTGATGTG AAACTGGCCT CCCAAGCCCT GATAACAAC     119
```

| ATG | GCC | AAC | GCC | CTG | GCC | AGC | GCC | ACT | TGC | GAG | CGC | TGC | AAG | GGC | GGC | 167 |
|---|---|---|---|---|---|---|---|---|---|---|---|---|---|---|---|---|
| Met | Ala | Asn | Ala | Leu | Ala | Ser | Ala | Thr | Cys | Glu | Arg | Cys | Lys | Gly | Gly | |
| 1 | | | | 5 | | | | | 10 | | | | | 15 | | |

| TTT | GCG | CCC | GCT | GAG | AAG | ATC | GTG | AAC | AGT | AAT | GGG | GAG | CTG | TAC | CAT | 215 |
|---|---|---|---|---|---|---|---|---|---|---|---|---|---|---|---|---|
| Phe | Ala | Pro | Ala | Glu | Lys | Ile | Val | Asn | Ser | Asn | Gly | Glu | Leu | Tyr | His | |
| | | 20 | | | | | 25 | | | | | 30 | | | | |

| GAG | CAG | TGT | TTC | GTG | TGC | GCT | CAG | TGC | TTC | CAG | CAG | TTC | CCA | GAA | GGA | 263 |
|---|---|---|---|---|---|---|---|---|---|---|---|---|---|---|---|---|
| Glu | Gln | Cys | Phe | Val | Cys | Ala | Gln | Cys | Phe | Gln | Gln | Phe | Pro | Glu | Gly | |
| | | 35 | | | | | 40 | | | | | 45 | | | | |

| CTC | TTC | TAT | GAG | TTT | GAA | GGA | AGA | AAG | TAC | TGT | GAA | CAT | GAC | TTT | CAG | 311 |
|---|---|---|---|---|---|---|---|---|---|---|---|---|---|---|---|---|
| Leu | Phe | Tyr | Glu | Phe | Glu | Gly | Arg | Lys | Tyr | Cys | Glu | His | Asp | Phe | Gln | |
| | 50 | | | | | 55 | | | | | 60 | | | | | |

| ATG | CTC | TTT | GCC | CCT | TGC | TGT | CAT | CAG | TGT | GGT | GAA | TTC | ATC | ATT | GGC | 359 |
|---|---|---|---|---|---|---|---|---|---|---|---|---|---|---|---|---|
| Met | Leu | Phe | Ala | Pro | Cys | Cys | His | Gln | Cys | Gly | Glu | Phe | Ile | Ile | Gly | |
| 65 | | | | | 70 | | | | | 75 | | | | | 80 | |

| CGA | GTT | ATC | AAA | GCC | ATG | AAT | AAC | AGC | TGG | CAT | CCG | GAG | TGC | TTC | CGC | 407 |
|---|---|---|---|---|---|---|---|---|---|---|---|---|---|---|---|---|
| Arg | Val | Ile | Lys | Ala | Met | Asn | Asn | Ser | Trp | His | Pro | Glu | Cys | Phe | Arg | |
| | | | | 85 | | | | | 90 | | | | | 95 | | |

| TGT | GAC | CTC | TGC | CAG | GAA | GTT | CTG | GCA | GAT | ATC | GGG | TTT | GTC | AAG | AAT | 455 |
|---|---|---|---|---|---|---|---|---|---|---|---|---|---|---|---|---|
| Cys | Asp | Leu | Cys | Gln | Glu | Val | Leu | Ala | Asp | Ile | Gly | Phe | Val | Lys | Asn | |
| | | | 100 | | | | | 105 | | | | | 110 | | | |

| GCT | GGG | AGA | CAC | CTG | TGT | CGC | CCC | TGT | CAT | AAT | CGT | GAG | AAA | GCC | AGA | 503 |
|---|---|---|---|---|---|---|---|---|---|---|---|---|---|---|---|---|
| Ala | Gly | Arg | His | Leu | Cys | Arg | Pro | Cys | His | Asn | Arg | Glu | Lys | Ala | Arg | |
| | | 115 | | | | | 120 | | | | | 125 | | | | |

| GGC | CTT | GGG | AAA | TAC | ATC | TGC | CAG | AAA | TGC | CAT | GCT | ATC | ATC | GAT | GAG | 551 |
|---|---|---|---|---|---|---|---|---|---|---|---|---|---|---|---|---|
| Gly | Leu | Gly | Lys | Tyr | Ile | Cys | Gln | Lys | Cys | His | Ala | Ile | Ile | Asp | Glu | |
| | 130 | | | | | 135 | | | | | 140 | | | | | |

| CAG | CCT | CTG | ATA | TTC | AAG | AAC | GAC | CCC | TAC | CAT | CCA | GAC | CAT | TTC | AAC | 599 |
|---|---|---|---|---|---|---|---|---|---|---|---|---|---|---|---|---|
| Gln | Pro | Leu | Ile | Phe | Lys | Asn | Asp | Pro | Tyr | His | Pro | Asp | His | Phe | Asn | |
| 145 | | | | | 150 | | | | | 155 | | | | | 160 | |

| TGC | GCC | AAC | TGC | GGG | AAG | GAG | CTG | ACT | GCC | GAT | GCA | CGG | GAG | CTG | AAA | 647 |
|---|---|---|---|---|---|---|---|---|---|---|---|---|---|---|---|---|
| Cys | Ala | Asn | Cys | Gly | Lys | Glu | Leu | Thr | Ala | Asp | Ala | Arg | Glu | Leu | Lys | |
| | | | | 165 | | | | | 170 | | | | | 175 | | |

| GGG | GAG | CTA | TAC | TGC | CTC | CCA | TGC | CAT | GAT | AAA | ATG | GGG | GTC | CCC | ATC | 695 |
|---|---|---|---|---|---|---|---|---|---|---|---|---|---|---|---|---|
| Gly | Glu | Leu | Tyr | Cys | Leu | Pro | Cys | His | Asp | Lys | Met | Gly | Val | Pro | Ile | |
| | | | 180 | | | | | 185 | | | | | 190 | | | |

| TGT | GGT | GCT | TGC | CGA | CGG | CCC | ATC | GAA | GGG | CGC | GTG | GTG | AAC | GCT | ATG | 743 |

```
       Cys Gly Ala Cys Arg Arg Pro Ile Glu Gly Arg Val Val Asn Ala Met
               195                 200                 205

GGC AAG CAG TGG CAT GTG GAG CAT TTT GTT TGT GCC AAG TGT GAG AAA         791
Gly Lys Gln Trp His Val Glu His Phe Val Cys Ala Lys Cys Glu Lys
    210                 215                 220

CCC TTT CTT GGA CAT CGC CAT TAT GAG AGG AAA GGC CTG GCA TAT TGT         839
Pro Phe Leu Gly His Arg His Tyr Glu Arg Lys Gly Leu Ala Tyr Cys
225                 230                 235                 240

GAA ACT CAC TAT AAC CAG CTA TTT GGT GAT GTT TGC TTC CAC TGC AAT         887
Glu Thr His Tyr Asn Gln Leu Phe Gly Asp Val Cys Phe His Cys Asn
                245                 250                 255

CGT GTT ATA GAA GGT GAT GTG GTC TCT GCT CTT AAT AAG GCC TGG TGC         935
Arg Val Ile Glu Gly Asp Val Val Ser Ala Leu Asn Lys Ala Trp Cys
            260                 265                 270

GTG AAC TGC TTT GCC TGT TCT ACC TGC AAC ACT AAA TTA ACA CTC AAG         983
Val Asn Cys Phe Ala Cys Ser Thr Cys Asn Thr Lys Leu Thr Leu Lys
        275                 280                 285

AAT AAG TTT GTG GAG TTT GAC ATG AAG CCA GTC TGT AAG AAG TGC TAT        1031
Asn Lys Phe Val Glu Phe Asp Met Lys Pro Val Cys Lys Lys Cys Tyr
    290                 295                 300

GAG ATT TCC ATT GGA GCT GAA GAA AAG ACT TAAGAAACTA GCTGAGACCT          1081
Glu Ile Ser Ile Gly Ala Glu Glu Lys Thr
305                 310

TAGGAAGGAA ATAAGTTCCT TTATTTTTC TTTTCTATGC AAGATAAGAG ATTACCAACA       1141

TTACTTGTCT TGATCTACCC ATATTTAAAG CTATATCTCA AAGCAGTTGA GAGAAGAGGA      1201

CCTATATGAA TGGTTTTATG TCATTTTTTT AAAAAAAAAA AAAAA                      1246
```

( 2 ) INFORMATION FOR SEQ ID NO:2:

( i ) SEQUENCE CHARACTERISTICS:
        ( A ) LENGTH: 314 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Asn Ala Leu Ala Ser Ala Thr Cys Glu Arg Cys Lys Gly Gly
 1               5                  10                  15

Phe Ala Pro Ala Glu Lys Ile Val Asn Ser Asn Gly Glu Leu Tyr His
            20                  25                  30

Glu Gln Cys Phe Val Cys Ala Gln Cys Phe Gln Gln Phe Pro Glu Gly
        35                  40                  45

Leu Phe Tyr Glu Phe Glu Gly Arg Lys Tyr Cys Glu His Asp Phe Gln
    50                  55                  60

Met Leu Phe Ala Pro Cys Cys His Gln Cys Gly Glu Phe Ile Ile Gly
65                  70                  75                  80

Arg Val Ile Lys Ala Met Asn Asn Ser Trp His Pro Glu Cys Phe Arg
                85                  90                  95

Cys Asp Leu Cys Gln Glu Val Leu Ala Asp Ile Gly Phe Val Lys Asn
            100                 105                 110

Ala Gly Arg His Leu Cys Arg Pro Cys His Asn Arg Glu Lys Ala Arg
        115                 120                 125

Gly Leu Gly Lys Tyr Ile Cys Gln Lys Cys His Ala Ile Ile Asp Glu
    130                 135                 140

Gln Pro Leu Ile Phe Lys Asn Asp Pro Tyr His Pro Asp His Phe Asn
145                 150                 155                 160

Cys Ala Asn Cys Gly Lys Glu Leu Thr Ala Asp Ala Arg Glu Leu Lys
```

|     |     |     |     |     |     |     | 165 |     |     |     |     | 170 |     |     |     |     | 175 |     |     |
|-----|-----|-----|-----|-----|-----|-----|-----|-----|-----|-----|-----|-----|-----|-----|-----|-----|-----|-----|-----|

Gly Glu Leu Tyr Cys Leu Pro Cys His Asp Lys Met Gly Val Pro Ile
                180                 185                 190

Cys Gly Ala Cys Arg Arg Pro Ile Glu Gly Arg Val Val Asn Ala Met
            195             200                 205

Gly Lys Gln Trp His Val Glu His Phe Val Cys Ala Lys Cys Glu Lys
        210             215             220

Pro Phe Leu Gly His Arg His Tyr Glu Arg Lys Gly Leu Ala Tyr Cys
225             230             235                         240

Glu Thr His Tyr Asn Gln Leu Phe Gly Asp Val Cys Phe His Cys Asn
                245             250             255

Arg Val Ile Glu Gly Asp Val Val Ser Ala Leu Asn Lys Ala Trp Cys
            260             265             270

Val Asn Cys Phe Ala Cys Ser Thr Cys Asn Thr Lys Leu Thr Leu Lys
        275             280             285

Asn Lys Phe Val Glu Phe Asp Met Lys Pro Val Cys Lys Lys Cys Tyr
    290             295                 300

Glu Ile Ser Ile Gly Ala Glu Glu Lys Thr
305             310

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..11

( x i ) SEQUENCE DESCRIPTION: SEQ ID NO:3:

Phe Lys Asn Asp Pro Tyr His Pro Asp His Phe
1               5                   10

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9

( x i ) SEQUENCE DESCRIPTION: SEQ ID NO:4:

Asn Ser Ser Tyr Phe Pro Gly Lys Leu
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..6

( x i ) SEQUENCE DESCRIPTION: SEQ ID NO:5:

Phe  Lys  Pro  Pro  Lys  Tyr
1                   5

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..24

( x i ) SEQUENCE DESCRIPTION: SEQ ID NO:6:

GGTGGCGACG ACTCCTGGAG CCCG                       24

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..24

( x i ) SEQUENCE DESCRIPTION: SEQ ID NO:7:

TTGACACCAG ACCAACTGGT AATG                       24

( 2 ) INFORMATION FOR SEQ ID NO:8:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..7

( x i ) SEQUENCE DESCRIPTION: SEQ ID NO:8:

AACATGG                                                              7

( 2 ) INFORMATION FOR SEQ ID NO:9:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..61

( x i ) SEQUENCE DESCRIPTION: SEQ ID NO:9:

| Cys<br>1 | Glu | Arg | Cys | Lys<br>5 | Gly | Gly | Phe | Ala | Pro<br>10 | Ala | Glu | Lys | Ile | Val<br>15 | Asn |
|---|---|---|---|---|---|---|---|---|---|---|---|---|---|---|---|
| Ser | Asn | Gly | Glu<br>20 | Leu | Tyr | His | Glu | Gln<br>25 | Cys | Phe | Val | Cys | Ala<br>30 | Gln | Cys |
| Phe | Gln | Gln<br>35 | Phe | Pro | Glu | Gly | Leu<br>40 | Phe | Tyr | Glu | Phe | Glu<br>45 | Gly | Arg | Lys |
| Tyr | Cys<br>50 | Glu | His | Asp | Phe | Gln<br>55 | Met | Leu | Phe | Ala | Pro<br>60 | Cys | | | |

( 2 ) INFORMATION FOR SEQ ID NO:10:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65

( x i ) SEQUENCE DESCRIPTION: SEQ ID NO:10:

| Cys<br>1 | His | Gln | Cys | Gly<br>5 | Glu | Glu | Phe | Ile | Ile<br>10 | Gly | Arg | Val | Ile | Lys<br>15 | Ala |
|---|---|---|---|---|---|---|---|---|---|---|---|---|---|---|---|
| Met | Asn | Asn | Ser<br>20 | Trp | His | Pro | Glu | Cys<br>25 | Phe | Arg | Cys | Asp | Leu<br>30 | Cys | Gln |
| Glu | Val | Leu<br>35 | Ala | Asp | Ile | Gly | Phe<br>40 | Val | Lys | Asn | Ala | Gly<br>45 | Arg | His | Leu |
| Cys | Arg<br>50 | Pro | Cys | His | Asn | Arg<br>55 | Glu | Lys | Ala | Arg | Gly<br>60 | Leu | Gly | Lys | Tyr |
| Ile<br>65 | | | | | | | | | | | | | | | |

( 2 ) INFORMATION FOR SEQ ID NO:11:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..58

( x i ) SEQUENCE DESCRIPTION: SEQ ID NO:11:

| Cys<br>1 | Gln | Lys | Cys | His<br>5 | Ala | Ile | Ile | Asp | Glu<br>10 | Gln | Pro | Leu | Ile | Phe<br>15 | Lys |
|---|---|---|---|---|---|---|---|---|---|---|---|---|---|---|---|
| Asn | Asp | Pro | Tyr<br>20 | His | Pro | Asp | His<br>25 | Phe | Asn | Cys | Ala | Asn<br>30 | Cys | Gly | Lys |
| Glu | Leu | Thr<br>35 | Ala | Asp | Ala | Arg | Glu<br>40 | Leu | Lys | Gly | Glu | Leu<br>45 | Tyr | Cys | Leu |
| Pro | Cys<br>50 | His | Asp | Lys | Met | Gly<br>55 | Val | Pro | Ile | | | | | | |

( 2 ) INFORMATION FOR SEQ ID NO:12:

( i ) SEQUENCE CHARACTERISTICS:

( A ) LENGTH: 59 amino acids
          ( B ) TYPE: amino acid
          ( C ) STRANDEDNESS: single
          ( D ) TOPOLOGY: linear ( i i ) MOLECULE TYPE: protein ( i x ) FEATURE:
          ( A ) NAME/KEY: Protein
          ( B ) LOCATION: 1..59

( x i ) SEQUENCE DESCRIPTION: SEQ ID NO:12:

```
Cys Gly Ala Cys Arg Arg Pro Ile Glu Gly Arg Val Val Asn Ala Met
1               5                   10                  15

Gly Lys Gln Trp His Val Glu His Phe Val Cys Ala Lys Cys Glu Lys
            20                  25                  30

Pro Phe Leu Gly His Arg His Tyr Glu Arg Lys Gly Leu Ala Tyr Cys
                35                  40                  45

Glu Thr His Tyr Asn Gln Leu Phe Gly Asp Val
        50                  55
```

( 2 ) INFORMATION FOR SEQ ID NO:13:

( i ) SEQUENCE CHARACTERISTICS:
          ( A ) LENGTH: 63 amino acids
          ( B ) TYPE: amino acid
          ( C ) STRANDEDNESS: single
          ( D ) TOPOLOGY: linear ( i i ) MOLECULE TYPE: protein ( i x ) FEATURE:
          ( A ) NAME/KEY: Protein
          ( B ) LOCATION: 1..63

( x i ) SEQUENCE DESCRIPTION: SEQ ID NO:13:

```
Cys Phe His Cys Asn Arg Val Ile Glu Gly Asp Val Val Ser Ala Leu
1               5                   10                  15

Asn Lys Ala Trp Cys Val Asn Cys Phe Ala Cys Ser Thr Cys Asn Thr
            20                  25                  30

Lys Leu Thr Leu Lys Asn Lys Phe Val Glu Phe Asp Met Lys Pro Val
                35                  40                  45

Cys Lys Lys Cys Tyr Glu Ile Ser Ile Gly Ala Glu Glu Lys Thr
        50                  55                  60
```

( 2 ) INFORMATION FOR SEQ ID NO:14:

( i ) SEQUENCE CHARACTERISTICS:
          ( A ) LENGTH: 11 amino acids
          ( B ) TYPE: amino acid
          ( C ) STRANDEDNESS: single
          ( D ) TOPOLOGY: linear ( i i ) MOLECULE TYPE: peptide ( i x ) FEATURE:
          ( A ) NAME/KEY: Peptide
          ( B ) LOCATION: 1..11

( x i ) SEQUENCE DESCRIPTION: SEQ ID NO:14:

```
Phe Lys Asn Ser Ser Tyr Phe Pro Gly Lys Leu
1               5                   10
```

( 2 ) INFORMATION FOR SEQ ID NO:15:

( i ) SEQUENCE CHARACTERISTICS:
          ( A ) LENGTH: 11 amino acids
          ( B ) TYPE: amino acid (C) STRANDEDNESS: single
(D) TOPOLOGY: linear (ii) MOLECULE TYPE: peptide (ix) FEATURE:
  (A) NAME/KEY: Peptide
  (B) LOCATION: 1..11

(xi) SEQUENCE DESCRIPTION: SEQ ID NO:15:

Phe Lys Pro Pro Lys Tyr His Pro Asp Val Pro
1               5                   10

(2) INFORMATION FOR SEQ ID NO:16:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..5
    (D) OTHER INFORMATION: /note="Where X appears, X =any amino acid"

(xi) SEQUENCE DESCRIPTION: SEQ ID NO:16:

Cys Xaa Xaa Cys His
1               5

(2) INFORMATION FOR SEQ ID NO:17:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..20
    (D) OTHER INFORMATION: /note="Where X occurs (3rd occurrence) X denotes any of 16-19 aa; where X occurs (10th occurrence) X denotes any of 16-21 aa; where X occurs (11th occurrence) X denotes any of 1-3 aa; where C appears (3rd and 4th occurrences) C denotes either cysteine or histidine; where C appears (8th occurrence) C denotes cysteine, histidine or aspartic acid"

(xi) SEQUENCE DESCRIPTION: SEQ ID NO:17:

Cys Xaa Xaa Cys Xaa Cys His Xaa Xaa Cys Xaa Xaa Cys Xaa Xaa Cys
1               5                   10                  15

Xaa Cys Xaa Cys
            20

AUTOANTIGEN, PINCH

BACKGROUND OF THE INVENTION

1. Field of the Invention

The invention relates generally to autoimmunity and specifically to a novel protein which contains an autoepitope and methods of detecting autoantibodies that bind to the autoepitope.

2. Description of Related Art

Binding of autoantibody to the senescent cell membrane is a major physiologic pathway for removal of senescent cells and is important in many disease states, such as sickle cell anemia and thalassemia (Turrini, et al., *J. Biol. Chem.*, 266:23611–23617, 1991). It has been determined that the chronology of RBC senescence is first, clustering of the integral membrane proteins (AE1) and glycophorin A (GPA), followed by autologous IgG binding, complement deposition, and phagocytosis. Clustering of AE1 and GPA within the RBC membrane leads to the close approximation of bound IgG molecules, resulting in complement activation, and deposition of complement components on the RBC surface. Subsequently, RBCs bind to phagocyte Fc and C3b receptors, and are engulfed and destroyed.

It has been shown that synthetic peptides corresponding to two autoepitopes of AE1, NSSYFPGKL (SEQ ID NO:4) and FKPPKY (SEQ ID NO:5), inhibit binding of IgG eluted from aged RBCs (Kay, M. M., et al., *Proc. Natl. Acad. Sci. U.S.A.*, 87:5734–5738, 1990). These peptides, when used together, produce greater inhibition of IgG binding to aged RBCs than either peptide used alone. However, since AE1 is present in all RBCs, young and old alike, some change in AE1 must occur to cause expression of an autoantigen that binds IgG. Obviously, identification and characterization the antoantigens which bind to IgG are important in understanding the mechanisms of phagocyte-mediated removal of senescent cells.

Identification of autoantigens is also essential to understanding and to intervention in the autoimmune response. For example, in autoimmune hemolytic anemia (AHA), autoantibody binding to autoantigen causes the clinical disorder, hemolysis. Yet such patients vary considerably with respect to this degree of hemolysis and response to treatment. Some individuals have IgG-coated RBCs (positive DAT) without hemolysis. Although some differences can be explained by variability in the autoantibody, such as IgG subclass, most differences are unexplained and must relate to the autoantigen detected.

Furthermore, autoantibodies are also found in other autoimmune disorders, in malignancies, in infectious diseases such as the acquired immunodeficiency syndrome, as well as in apparently healthy individuals. Clinically-relevant autoantigens have been cloned in several autoimmune disorders. For example, clones expressing the La autoantigen of Sjogren's syndrome (Chambers, et al., *J. Biol. Chem.*, 263:18043–18051, 1988) the M2 mitochondrial autoantigen of primary biliary cirrhosis (Coppel, et al., *Proc. Natl. Acad. Sci., U.S.A.*, 85:7317–7321, 1988) the Sm and p70 (KU) autoantigens of systemic lupus erythematosis (Ohosone, et al., *Proc. Natl. Acad. Sci, U.S.A.*, 86:4249–4253, 1989; Reeves, et al., *J. Biol. Chem.*, 264:5047–5052, 1989).

At present, complex native autoantigens such as RBC membrane proteins are used to detect and characterize RBC autoantibodies. However, since only limited regions of molecules appear to be involved in an immune response, central to understanding the immune response is understanding the nature of antigenic determinants that stimulate the immune response.

Therefore, identification of autoantigens and the polynucleotides encoding them is important in understanding the mechanisms involved in the removal of senescent cells and the autoimmune response. The identity of such autoantigens is also important in development of diagnostics and therapeutics for intervention or inhibition of an undesired immune response. The present invention identifies a novel autoantigen, PINCH, that binds IgG specific, inter alia, for aged cells. Thus, the PINCH autoantigen is useful for the in vitro and in vivo removal from susceptible individuals of autoantibodies which bind aged RBCs and other cells, thereby increasing the lifespan of such cells and, at least for aged RBCs, reducing the need for transfusion.

SUMMARY OF THE INVENTION

The present invention provides a novel PINCH polypeptide, a polynucleotide sequence which encodes the polypeptide, and antibodies which bind to the protein. The PINCH protein contains an autoantigen which binds to autoantibodies found in individuals with autoimmune disease, such as hemolytic anemia, and autoantibodies involved in the removal of senescent cells.

Thus, in one embodiment, the invention provides a method for detecting an autoantibody in a sample that binds to an epitope contained in SEQ ID NO:2 which comprises contacting the sample suspected of having an autoantibody to SEQ ID NO:2 with the epitope under conditions sufficient for forming an immune complex between the epitope and the autoantibody and determining whether an immune complex is formed, wherein formation of the complex is indicative of the presence of an autoantibody. The autoepitope is associated with such diseases as hemolytic anemia and also involved in the removal of aged RBCs cells.

In another embodiment, the invention provides a method of isolating an autoantibody that binds to an epitope contained in SEQ ID NO:2 from a sample comprising binding the autoepitope to a solid support and contacting the sample suspected of having an autoantibody with the autoepitope bound to the solid support under conditions that allow the autoantibody and autoepitope to form an immune complex, thereby removing the autoantibody from the sample. Preferably, this method is used to remove autoantibodies from blood samples. If desired, the autoantibodies can be eluted from the complex and used, for example, in immunologic assays to detect antigens which possess SEQ ID NO:2.

In yet another embodiment, the invention provides a method of treating an autoimmune disease associated with an autoantibody that binds to SEQ ID NO:2 which comprises contacting the autoantibody with a reagent that binds to the autoantibody.

BRIEF DESCRIPTION OF THE DRAWINGS

FIG. 1 shows the sequencing strategy used to obtain the full nucleotide sequence of the PINCH ORF. ATG and TAA show the location of the initiator and termination codons respectively. EcoRI indicates the site of the EcoRI restriction site in the ORF. cPINCH #1–#6 represent the 6 independently isolated partial cDNAs. RACE #1-RACE #4 represent the PCR products obtained using the RACE procedure.

FIG. 2 shows the nucleotide sequence of the PINCH ORF and its translated amino acid sequence. The five LIM domains are underlined. The location of a potential N-glycosylation site is indicated by the diamond symbol. Asterisks appear above the three cytochrome c heme binding motifs (CXXCH) SEQ ID NO:16. The amino acids that form the potential zinc finger of the C4 type in the linker between the second and third LIM domains are shown in italics. A dotted line appears above the PINCH autoepitope.

FIG. 3 shows graphs of hydrophilicity, surface probability, flexibility, antigenic index, and secondary structure predictions for PINCH polypeptide. Numbers under each graph indicate PINCH amino acid residues.

DETAILED DESCRIPTION OF THE INVENTION

Figure 4:
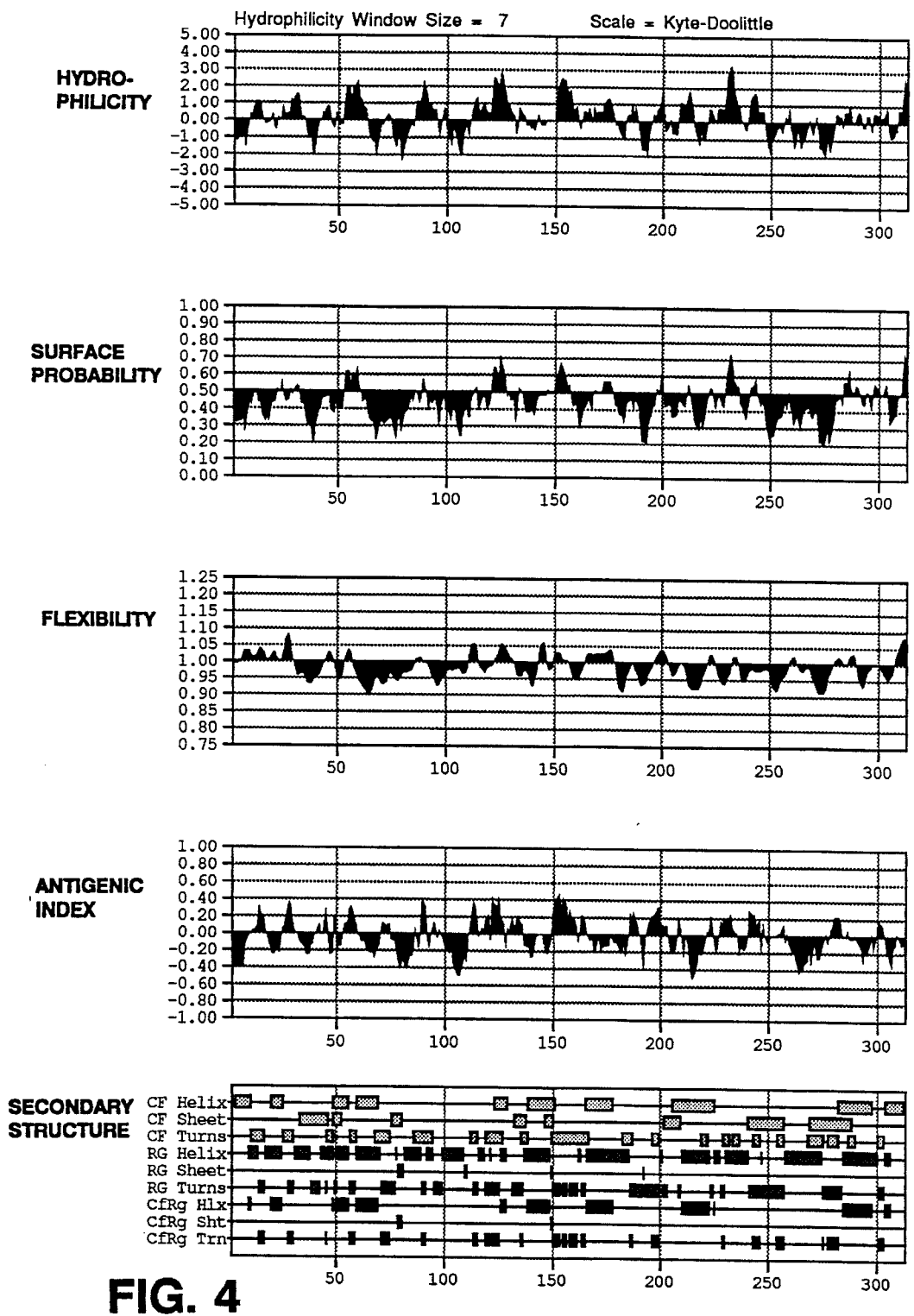
FIG. 4 shows models of the structure of PINCH. The amino and carboxyl termini are indicated by NH2 and COOH respectively. The location of the cytochrome c heme binding motifs (CXXCH) SEQ ID NO:16 are shown by asterisks, and of each of the four prolines in the zinc-coordinating finger bases by P. The arrowed line shows the location of the PINCH autoepitope. The numbers under each model are the amino acid residues from the amino terminus. Underlined numbers indicate the PINCH autoepitope.

The present invention provides a novel polypeptide called PINCH (particularly interesting new Cys-His protein). PINCH is homologous to the LIM family of proteins and appears to function as a binding protein via its zinc fingers. This new LIM family protein, PINCH, however, is unique in the LIM family having five LIM domains rather than one to three domains. In addition, the LIM motif is modified in this protein. For example, instead of a $C_2HC$ type first finger in each finger doublet, $C_2H_2$ type fingers are substituted in the third and fourth LIM domains, and a $C_4$ type finger is substituted in the fifth LIM domain. The modified LIM motif is: $CX_2CX_{16-19}C/HX_2C/HX_2CX_2CX_{16-21}CX_{1-3}C/H/D$ (SEQ ID NO:17). Furthermore, PINCH is unique among LIM proteins in that it has all three possible terminal zinc-coordinating residues in the second finger of its LIM domains (three cysteine, one histidine, and one aspartate). Four proline residues occur in the zinc-coordinating finger bases ($CX_2C$, etc.) of the second and third LIM domains, and both domains end with cysteine. Since many LIM domain proteins in the proline-containing, terminal cysteine group are cytoplasmic, and function in protein-protein interactions, such as zyxin and CRP, it is probable that PINCH functions in a similar way. However, the presence of proline in the finger base may result in a different finger configuration, and/or differences in metal coordination that may correlate with function.

PINCH may play a role in the IgG-mediated removal of aged cells by phagocytes. PINCH polypeptide contains elements that may bind zinc, iron, sulfur or other metals, or heme. PINCH may therefore be responsive to changes in transition metal and/or heme concentration that occur with senescence. There are many ionic changes in the senescent RBC (Cameron, et al., *Cell Biol Int.* 17:93, 1993). It is possible that PINCH function is associated with these changes. Although not wanting to be bound by any particular theory, it is believed that PINCH participates directly in the process of aged cell removal, perhaps responding to such factors as redox changes in the cell with aging, changes in metal concentration, autoantibody binding, or clustering of membrane proteins in senescent cells. Alternatively, PINCH may serve as an immunogen for the production of IgG autoantibodies with crossreacting specificity for epitopes on AE1 and/or other molecules.

The primary biological activity of PINCH is its ability to bind antibody. Specifically, it is known that PINCH binds autoantibody to aged RBCs. The PINCH autoepitope, FKNDPYHPD (SEQ ID NO:3), is located in the first finger of the third LIM domain from the amino terminus. The first three amino acids in the PINCH autoepitope, FKN, are similar to the first amino acid of the AE1 593–601 autoepitope and the two preceding amino acids, and the last four amino acids in the PINCH autoepitope, YHPD (last 4 amino acids of SEQ ID NO:3), are similar to the last amino acid in the AE1 813–818 autoepitope and the following three amino acids. Since synthetic peptides corresponding to these two autoepitopes of AE1, NSSYF-PGKL (SEQ ID NO:4) and FKPPKY (SEQ ID NO:5), synergistically inhibit binding of IgG eluted from aged RBCs, the PINCH autoepitope is predicted to also be surface-exposed and to have high antigenicity via algorithms based on amino acid sequence (See FIG. 4).

PINCH protein is useful both in vitro or in vivo. For example, PINCH autoantigen is useful for in vitro studies such as purification, identification and quantitation of autoantibodies. Recombinant PINCH autoantigen can be used to characterize the specificities of RBC autoantibodies in autoimmune hemolytic anemia (AHA) and in patients with a positive direct antiglobulin test (DAT) without hemolysis, and to characterize the specificities of pathologic autoantibodies that cause clinical hemolysis as well as physiologic autoantibodies that mediate removal of aged RBCs by phagocyte. Such information could be used to determine the relatedness of these two families of antibodies. Additionally, PINCH autoantigen is useful for in vivo or ex vivo removal of autoantibodies with specificity for aged RBCs, increasing RBC lifespan and thereby reducing the need for transfusion. PINCH autoantigen is also useful in vitro and in vivo for identification of autoantibodies which bind to a PINCH epitope on other cell types as well.

The term "substantially purified" as used herein refers to PINCH which is substantially free of other proteins, lipids, carbohydrates or other materials with which it is associated in its natural environment. One skilled in the art can purify PINCH using standard techniques for protein purification. The substantially pure PINCH polypeptide will yield a single major band on a nonreducing polyacrylamide gel. The purity of the PINCH polypeptide can also be determined by amino-terminal amino acid sequence analysis. The term "isolated" means any PINCH polypeptide of the present invention, or any gene encoding a PINCH polypeptide, which is essentially free of other polypeptides or genes, respectively, or of other contaminants with which the PINCH polypeptide or polynucleotide might normally be found in nature.

PINCH polypeptide includes functional fragments of the polypeptide, as long as the activity of PINCH remains. Smaller peptides containing a biological activity of PINCH, such as binding to autoantibody, are included in the invention. Preferably the peptide of the invention is the amino acid sequence epitope of SEQ ID NO:3.

As used herein, the term "synthetic peptide" denotes a peptide which does not comprise an entire naturally occurring protein molecule. These peptides are "synthetic" in that they may be produced by human intervention using such techniques as chemical synthesis, recombinant genetic techniques, or fragmentation of whole antigen or the like. "Immunogenic" means that the peptides of the invention can participate in an immune response. This participation can be, for example, either passive or active participation.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention includes a functional polypeptide, PINCH, and functional fragments thereof. As used herein, the term "functional polypeptide" refers to a polypeptide which possesses a biological function or activity which is identified through a defined functional assay, and which is associated with a particular biologic, morphologic, or phenotypic alteration in the cell. The biological function, for example, can vary from a polypeptide fragment as small as an epitope to which an antibody molecule can bind, such gas SEQ ID NO:3, to a large polypeptide. A "functional polynucleotide" denotes a polynucleotide which encodes a functional polypeptide as described herein.

Minor modifications of the PINCH primary amino acid sequence may result in proteins which have substantially equivalent activity as compared to the PINCH polypeptide described herein. Such modifications may be deliberate, as by site-directed mutagenesis, or may be spontaneous. All of the polypeptides produced by these modifications are included herein as long as the epitope of PINCH is present. Further, deletion of one or more amino acids can also result in a modification of the structure of the resultant molecule without significantly altering its activity or ability to bind autoantibody. This can lead to the development of a smaller active molecule which would have broader utility. For example, it is possible to remove amino or carboxy terminal amino acids which may not be required for PINCH activity. Such modifications are embraced by the present invention.

The PINCH polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The sequence of the cDNA for PINCH contains an open reading frame (ORF) of 942 nucleotides with an initiator codon subsequence AACATGG (SEQ ID NO:8) at the 5' region. The ORF encodes a 314 amino acid polypeptide with a calculated molecular mass of 35,799 kDa. PINCH contains 33 cysteines (10% of the total number of amino acids) and 16 histidines (5%) with an estimated pI of 8.47. Analysis of the first 100 and remaining 214 residues separately showed that the first 100 residues have a pI of 5.37 and are enriched in phenylalanine (10%) and glutamic acid (10%), while the remaining 214 residues have a pI of 9.23, and are enriched in lysine (9%). A potential N-glycosylation site is present at residue 87 from the amino terminus. Three cytochrome c heme binding motifs are present beginning at residues 118, 135, and 181 in the second and third LIM domains, and a potential zinc finger of the $C_4$ type is present beginning at residue 181, encompassing the linker between the second and third LIM domains. There is no hydrophobic region of sufficient length to suggest the presence of a membrane-spanning domain. There are multiple surface-exposed regions, including a number with predicted high antigenicity.

The invention also provides polynucleotides which encode the PINCH polypeptide of the invention and the synthetic peptide of SEQ ID NO:3. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding PINCH is the sequence of SEQ ID NO:1.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981; Maniatis, et al., *Molecular Cloning: A Laboratory Manual,* Cold Spring Harbor Laboratory, Cold Spring Harbor, N.Y., 1989).

The development of specific DNA sequences encoding PINCH can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for PINCH polypeptide having at least one epitope, using antibodies specific for PINCH. Such antibodies can be either polyclonally or monoclonally derived and used to detect expression product indicative of the presence of PINCH cDNA.

A polynucleotide sequence can be deduced from the genetic code, however, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of PINCH results in a functional polypeptide (at least, in the case of the sense polynucleotide strand), all degenerate nucleotide sequences are included in the invention.

The polynucleotide sequence for PINCH also includes sequences complementary to the polynucleotide encoding PINCH (antisense sequences). Antisense nucleic acids are DNA or RNA molecules that are complementary to at least a portion of a specific mRNA molecule (Weintraub, *Scientific American,* 262:40, 1990). The invention embraces all antisense polynucleotides capable of inhibiting production of PINCH polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target PINCH-producing cell. The use of antisense methods to inhibit the translation of genes is well known in the art (Marcus-Sakura, *Anal. Biochem.,* 172:289, 1988).

Preferably the PINCH polynucleotide of the invention is derived from a vertebrate, and most preferably from human, monkey, rat, mouse, dog, cow, rabbit, and chicken. Screening procedures which rely on nucleic acid hybridization make it possible to isolate PINCH nucleotide sequence from any organism, provided the appropriate probe is available.

In a preferred embodiment, cDNA sequences of the invention are obtained by antibody screening of human fetal liver expression library. Preferably, the screening antibodies are autoantibodies. Most preferably, the autoantibodies are from aged red blood cell eluate.

The PINCH polypeptide of the invention can also be used to produce antibodies which are immunoreactive or bind to epitopes of the PINCH polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256: 495, 1975; *Current Protocols in Molecular Biology,* Ausubel, et al., ed., 1989).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. An "autoepitope" is an antigenic determinant to which the paratope of an autoantibody binds. Therefore, an autoepitope may stimulate the production of antibodies which do not recognize the autoepitope as "self".

Antibodies which bind to the PINCH polypeptide of the invention can be prepared using an intact polypeptide or fragments containing small peptides of interest as the immunizing antigen. The polypeptide or a peptide such as SEQ ID NO:3 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit). Techniques for producing an immune response to peptides are well known in the art.

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et a., Unit 9, *Current Protocols in Immunology*, Wiley Interscience, 199, incorporated by reference).

It is also possible to use the anti-idiotype technology to produce monoclonal antibodies which mimic an epitope. For example, an anti-idiotypic monoclonal antibody made to a first monoclonal antibody, such as an autoantibody, will have a binding domain in the hypervariable region which is the "image" of the epitope bound by the first monoclonal antibody. Thus, in the present invention, an anti-idiotype antibody produced from an autoantibody which binds to the polypeptide or peptide of the invention can bind to the site on the autoantibody which binds to PINCH, thereby preventing the autoantibody from binding to PINCH.

Polynucleotide sequences encoding the polypeptide (SEQ ID NO:2) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the PINCH polynucleotide sequences may be inserted o into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (Eukaryotic Viral Vectors, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The invention provides a method for detecting an autoantibody that binds to an epitope contained in SEQ ID NO:2 in a sample comprising contacting the sample suspected of having an autoantibody with the epitope under conditions sufficient for forming an immune complex between the epitope and the autoantibody and determining whether an immune complex is formed, wherein formation of the complex is indicative of the presence of an autoantibody. For example, a sample suspected of containing autoantibody is obtained from a subject, then contacted with at least one epitope contained in SEQ ID NO:2, such as FKNDPYHPD (SEQ ID NO:3), under conditions sufficient to allow formation of an immune complex between the autoantibody and the epitope of the invention. The formation of the immune complex is then determined. The condition is "sufficient" if an immune complex can be formed between the autoantibody and the epitope of the present invention. The presence of an immune complex is determined by methods well known in the art, such as immunoassay, radioimmunoassay (RIA), ELISA and immunofluorescence. The PINCH polypeptide or SEQ ID NO:3 of the invention is particularly suited for use in immunoassays in which it can be utilized in liquid phase or bound to a solid phase carrier. In addition, PINCH polypeptide or SEQ ID NO:3 used in these assays can be detectably labeled in various ways.

Examples of immunoassays which can utilize the PINCH polypeptide or SEQ ID NO:3 of the invention are competitive and non-competitive immunoassays in either a direct or indirect format. Examples of such immunoassays are the radioimmunoassay (RIA), the sandwich (immunometric assay) and the Western blot assay. Detection of antibodies which bind to the PINCH polypeptide or SEQ ID NO:3 of the invention can be done utilizing immunoassays which run in either the forward, reverse, or simultaneous modes, including immunohistochemical assays on physiological samples. The concentration of PINCH polypeptide or SEQ ID NO:3 which is used will vary depending on the type of immunoassay and nature of the detectable label which is used. However, regardless of the type of immunoassay which is used, the concentration of PINCH polypeptide or SEQ ID NO:3 utilized can be readily determined by one of ordinary skill in the art using routine experimentation.

The PINCH polypeptide or SEQ ID NO:3 and PINCH polypeptide or SEQ ID NO:3 fragments of the invention can be bound to many different carriers and used to detect the presence of antibody specifically reactive with the polypeptide. Alternatively, the carrier-bound PINCH polypeptide or SEQ ID NO:3 and PINCH polypeptide or SEQ ID NO:3 fragments can be used therapeutically for extracorporeal absorption of autoimmune antibodies in patients having, or at risk of having, PINCH polypeptide or SEQ ID NO:3 binding antibody-associated disorders. Methods for such ex vivo treatments are well known in the art (see for example, U.S. Pat. No. 5,037,649, herein incorporated by reference). For example, the method of the present invention may utilize an immunoadsorbent column having an immunoadsorbent material therein which is suitable for the extra corporeal treatment of a patient's plasma to remove IgG and IgG-complexes therefrom. The extra corporeal treatment may be provided by continuously removing a patient's blood, separating the blood cells therefrom, treating the blood plasma in the immunoadsorbent column to remove the IgG and IgG-complexes, and mixing and returning the treated plasma and blood cells directly to the patient. Alternatively, after the blood has been removed and the blood cells separated, the blood cells may be directly reinfused into the patient. The separated plasma may be collected, treated in the immunoadsorbent column of the present invention, again collected and then returned to the patient at a later time.

Suitable immunoadsorbent materials comprise receptors bound to a solid phase matrix, where the receptors are capable of specifically binding immune complexes. Useful receptors include protein A, anti-lg antibodies, C1q, and antibodies capable of binding auto-antibodies that bind to an epitope in PINCH. A preferred immunoadsorbent material of the present invention comprises protein A covalently coupled to a solid-phase silica matrix under particular conditions which have been found to maximize activity of the protein A and binding capacity of the column while minimizing leakage of the protein A and other substances from the column during use.

Protein A is a cell surface protein which is isolated from particular strains of *Staphylococcus aureus* and able to bind free IgG and IgG-complexes. IgG-complexes are antigen-IgG complexes which circulate in patient serum and are not removed by the normal phagocytic mechanisms of the immune system. As stated above, removal of such circulating IgG-complexes is useful in the treatment of a variety of disorders, including autoimmune disorders and cancer. The immunoadsorbent material of the present invention will have a binding capacity of at least 5 mg IgG/gm adsorbent, usually 7 mg/gm or greater. The immunoadsorbent system of the present invention allows removal of up to about 750 to 1500 mg of the circulating IgG-complexes, usually about 1000 mg by treatment of the plasma.

Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding PINCH polypeptide or SEQ ID NO:3, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Preferably, the autoantibody which is detected or identified by the method of the invention is a RBC autoantibody associated with autoimmune hemolytic anemia. The autoantibody may also be a RBC autoantibody found in patients with a positive direct antiglobulin test without hemolysis. Alternatively, it may be a specific physiologic autoantibody that mediates removal of aged RBCs by phagocytes. Therefore, this method is useful in characterizing the specificities of RBC autoantibodies in autoimmune hemolytic anemia and in patients with a positive direct antiglobulin test without hemolysis.

The method of the invention is not limited to an epitope found on an RBC. The epitope, such as SEQ ID NO:3, may also be associated with tissue in autoimmune diseases such as lupus erythematosus, multiple sclerosis, Peyronies disease, asthma, type 1 insulin-dependent diabetes mellitus, inflammatory bowel disease, dermatitis, meningitis, thrombotic thrombocytopenic purpura, Sjögren's syndrome, encephalitis, uveitic, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis and Addison's disease.

The invention also discloses a method for isolating an autoantibody that binds to an epitope contained in SEQ ID NO:2 of the present invention from a sample comprising binding the autoepitope to a solid support contacting the sample suspected of having an autoantibody with the autoepitope bound to the solid support under conditions that allow the autoantibody and autoepitope to form an immune complex, thereby removing the autoantibody from the sample. For example, the autoantibody can be removed by passing the sample from an affinity column having the epitope of SEQ ID NO:2 bound under conditions which allow the antibody to bind to the column. In a preferred embodiment, the autoantibody is specific for aged RBCs. Preferably, the sample is a blood sample. Therefore, an autoantibody with specificity for aged RBCs may be removed from the blood sample by using this method for use in vivo where the blood can be reinfused into a subject. As a result, the RBC lifespan can be increased thereby reducing the need for frequent transfusions. Alternatively, the treatment removal of autoantibodies to aged RBCs for in vitro use is important for prolonging the life of blood in the blood banks. Alternatively, any sample, including serum, urine, saliva and tissue from any organ can be used as a source of autoantibody in the method of the invention.

The invention also discloses a method of treating an autoimmune disease associated with an autoantibody that binds to SEQ ID NO:2 which comprises contacting the autoantibody with a reagent that binds to the autoantibody. The autoimmune disease may be hemolytic anemia caused by RBC autoantibodies, for example. The term "treating" denotes a lessening of the detrimental effect of the autoantibody-induced response in the patient receiving therapy. The effect would be achieved by using a reagent to bind to and suppress the function of the autoantibody. In a preferred embodiment, the reagent comprises the PINCH protein as in SEQ ID NO:2 or the peptide epitope of SEQ ID NO:3 of the present invention thereby acting as competitive inhibitors.

When an autoimmune disorder is associated with autoantibodies that bind to an epitope contained in SEQ ID NO:2, a peptide such as SEQ ID NO:3 may be used as a competitive inhibitor of the natural cell-associated PINCH protein. For example, peptides with the sequence, FKNDPYHPD (SEQ ID NO:3), can be introduced to a subject and would compete for the site on the antibody that typically binds to the same epitope on the cell-associated PINCH protein. These peptides would therefore prevent a cell from being removed or killed by the autoantibody. In addition, a PINCH autoantibody anti-idiotype antibody which binds to a monoclonal autoantibody which binds to an epitope contained within SEQ ID NO:2, may also be used in the therapeutic method of the invention.

The peptides of the invention can be used singularly, in mixtures, or as multimers such as aggregates, polymers, and the like. Thus, the invention embraces synthetic peptides which comprise one or more of the same, or different, peptides of the invention to produce a homogeneous or heterogeneous polymer with respect to the particular peptides of the invention which are contained therein. Appropriate techniques for producing various mixtures, aggregates, multimers and the like will be known to those of skill in the art. For example, the invention would include a polypeptide comprising SEQ ID NO:2 or a peptide comprising SEQ ID NO:3 or both, wherein SEQ ID NO:2 and/or SEQ ID NO:3 are linked directly or indirectly, for example, by using a spacer or linker moiety. Techniques for utilizing spacer or linker moieties are well known in the art.

One of skill in the art would be able to determine the dose of peptide (e.g., SEQ ID NO:3) or polypeptide (e.g., SEQ ID NO:2) administered to a subject based on such factors as avoiding that amount of polypeptide or peptide that would stimulate an antibody response to the peptide or polypeptide. It would be a matter of routine to determine a high zone and low zone tolerance dose.

The anti-idiotype antibodies or peptide of the invention can be administered parenterally by injection or by gradual infusion over time. The antibodies or peptide of the invention can be administered intravenously, intraperitoneally, intramuscularly, subcutaneously, intracavity, or transdermally.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Delivery of PINCH polypeptide or peptide can be achieved using polynucleotide inserted in a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a PINCH sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the PINCH polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for PINCH or peptide polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Polypeptide analogs of the present invention may be designed which will compete for recognition of self-antigens at the level of antigen presentation or induce anergy in T cells, due to a lack of a costimulatory signal. Since MHC molecules contain a single peptide binding site, it is possible to design polypeptides which will bind with high affinity to disease-associated MHC molecules, but will not activate disease-causing T-helper cells. Such polypeptides act as antagonists for self-antigen recognition. Precedent for such an approach arises from observation that a mouse lysozyme polypeptide, itself non-immunogenic, can compete for MHC binding with an immunogenic polypeptide from hen-egg white lysozyme and thereby reduce T cell activation by that polypeptide (Adorini, et al., *Nature,* 334:623–625, 1988) as well as studies using T-cell receptor peptides to block formation of complex between T-cells, autoantigen and MHC (Howell, et al., *Science,* 246:668, 1989). Similarly, such a therapeutic approach for screening effective polypeptide analogs has been utilized in such autoimmune diseases as experimental autoimmune encephalomyelitis (EAE) (Wraith, et al., *Cell,* 59:248, 1989; Urban, et al., *Cell,* 59:257, 1989).

In an autoimmune disease, the immune tolerance system of the patient fails to recognize self antigens and, as a consequence of this loss of tolerance, brings the force of the immune system to bear on tissues which express the antigen. According to the method of the invention, a patient with autoimmune disease may be treated with an immunosuppressive agent to deplete the thymic medulla of resident APCs, such as dendritic cells, then, preferably, the immunosuppressive agent is withdrawn. Following withdrawal of the immunosuppressive agent, APCs from other regions of the patient's body which are tolerogenic for the self antigens previously targeted by the autoimmune disease re-populate the thymus and restore immunologic homeostasis by regulating autoimmune reactions and arrest the autoimmune disease. If the loss of selftolerance results from defective APCs, then either new APCs could be infused or the host's APCs (or corresponding precursor cells) could be harvested and modified before reinfusing into the patient. For example, genetic engineering could replace an HLA-DQ known to be defective in inducing tolerance with an acceptable HLA-DQ. In this situation, the new or altered APCs would be infused at the end of administration of the immunosuppressive agent. In each situation, the recruitment of DC into the thymus could be enhanced by administering a thymus regenerating agent.

The following examples are intended to illustrate but not limit the invention. While they are typical of those that might be used, other procedures known to those skilled in the art may alternatively be used.

The abbreviations used in Examples include:

RBC: red blood cell

PINCH: particularly interesting new Cys-His protein

AEI: anion exchange protein bp: base pair(s)

PCR: polymerase chain reaction

UT: untranslated

ORF: open reading frame

RACE: rapid amplification of 5' cDNA ends.

EXAMPLE 1

IDENTIFICATION AND ISOLATION OF CLONES EXPRESSING PINCH

To identify and isolate clones expressing PINCH, RBC autoantibody-containing eluates were used to screen an expression library. RBC autoantibody-containing eluates were prepared from direct antiglobulin test negative human RBCs that were coated in vivo with RBC autoantibody. The expression library was a human fetal liver library.

1. Human autoantibody to aged cells

The antibody eluate used for library screening was prepared from a 50 day old unit of blood drawn from a normal human blood donor. Human RBCs were obtained following a protocol approved by the University of California San Diego Human Subjects Committee. The unit was drawn in citrate/phosphate/dextrose/adenine and stored at 4° C. The direct antiglobulin test on the unit was negative. The autoantibody eluate was prepared using the acid-stromal method as described (Jenkins D. E. and Moore, W. H. *Transfusion*

17:110–114, 1977; Rearden A., et al., *Transfusion*, 23:248–25, 1983). Briefly, RBC membranes were isolated by digitonin lysis of RBCs, washed, and eluted in acidic buffer. Neutral pH was rapidly restored in the eluate, which was then stored at −70° C. until used. The eluate buffer was changed to that used for immunoscreening by dialysis. In general, eluates prepared by the acid stromal elution method contain autologous IgG, globin, and RBC membrane proteins, including AE1 and actin (Rearden, A., et al., *Transfusion*, 23:248–25, 1983). The autoantibody eluate used for immunoscreening contained 500 ug/ml protein as measured by optical density at 280 nm, and 17 ug/ml IgG as measured by nephelometry. Eluates were also prepared from in vitro-aged RBCs from two additional unrelated normal blood donors and used for confirmatory testing.

2. Expression Library Screening and cDNA sequencing

A human fetal liver library was obtained from Clontech Laboratories. The manufacturer stated that the library contained more than 1 million independent clones in the λgt11 expression vector. The library was plated in its entirety on *E. coli* strain Y1090 and recombinant protein expression induced with isopropyl-β-thiogalactopyranoside. For immunoscreening, nitrocellulose filters were blocked with 3% gelatin for 30 minutes at room temperature, and incubated with a one in four dilution of the autoantibody eluate overnight at room temperature. Positive plaques were identified by reaction with alka-line-phosphatase-conjugated antihuman IgG (goat) (Lambda Lift kit, BioRad Laboratories). Secondary and tertiary screens with the same autoantibody eluate were performed on the positive plaques to confirm reproducible binding of the autoantibody eluate and to obtain plaque-purified clones. Autoantibody eluates prepared from in vitro-aged RBCs from two additional normal blood donors were also reacted with the positive plaques to show that the isolation of cDNAs using the autoantibody eluate from the first blood donor was not fortuitous.

cDNA inserts were amplified with λgt11-specific primers. The forward primer was 5' GGTGGCGACGACTCCTG-GAGCCCG 3' (SEQ ID NO:6), and the reverse primer was 5' TTGACACCAGACCAACTGGTAATG 3' (SEQ ID NO:7). The PCR reaction was carried out using a Perkin Elmer Cetus Gene Amp™ DNA amplification kit. Briefly DNA from 1/50th of a plaque was added to a final volume of 50 µl of 10 mM Tris-HCl, pH 8.3, 50 mM KCl, 1.5 mM MgCl$_2$, 0.2 mM each dATP, dTTP, dGTP, and dCTP, 25 picomoles of each primer and 1.25 units of DNA polymerase (AmpliTaq). Following an initial single amplification cycle of denaturation for 2 minutes at 94° C., annealing for one minute at 60° C., and polymerization for one minute at 72° C., amplification of insert DNA was repeated 30 times under the conditions of denaturation for 1 minute at 94° C., annealing for 1.5 minutes at 60° C., and polymerization for 2 minutes at 72° C. in a Perkin Elmer Cetus DNA Thermal Cycler. Amplification was followed by a primer extension step at 72° C. for 7 minutes.

PCR products were separated by electrophoresis on 1% agarose gel, recovered and purified with GeneClean (Bio 101). PCR products were sequenced directly in both directions using the fmol™ cycle sequencing kit from Promega Corporation and custom oligonucleotide primers synthesized by Midland Certified Reagent Company. Sequencing primers were 5' end-labeled with [γ-$^{32}$P]ATP using T4 polynucleotide kinase. Amplification conditions for sequencing were an initial denaturation for 2 minutes at 95° C., followed by 30 cycles of denaturation for 1 minute at 95° C., and annealing/extension for 40 seconds at 70° C. Sequencing reactions were separated on 5% denaturing polyacrylamide gels, and the gels were dried and exposed to X-ray film for one to three days.

Thirteen cDNA clones, varying in insert size from 800 to 2500 bp, were isolated from the human fetal liver expression library by immunoscreening more than 1 million plaques with autoantibody eluate. Sequencing revealed that six of the thirteen clones, with insert sizes from 1000 to 1800 bp, contained an identical ORF of 717 bp, and differed from one another solely in the length of their 3'-UT regions. The ORF was in frame with the vector beta-galactosidase To obtain additional 5' nucleotide sequences, the RACE procedure was employed (see Frohman M. A., *Methods Enzymol.*, 218:340–356, 1993). A human peripheral blood leukocyte library especially prepared for the RACE procedure (5'-RACE-Ready™ cDNA, Clontech) was first primed with the anchor primer provided by the manufacturer, and a custom primer specific for a known 5' sequence of the ORF. The resulting PCR product was then reprimed with the anchor primer and a nested custom primer specific for a known sequence of the ORF, 5' to the sequence used for the initial specific priming. The reaction mixture for the RACE PCR was the same as described above for the PCR of cDNA inserts, except it contained 10 picomoles of the anchor primer, 25 picomoles of the custom primer, 2 ul of the 5'-RACE-Ready™ cDNA, and 2.5 units of AmpliTaq DNA polymerase. The PCR cycling parameters were denaturation for 1 minute at 94° C., annealing for 1 minute at 60° C., and polymerization for 2 minutes at 72° C. Amplification for 30 cycles was followed by a primer extension step at 72° C. for 7 minutes. PCR reactants and cycling parameters were the same for the secondary PCR except that the secondary PCR used 2 ul from the primary PCR as the source for template DNA, a dilution of 1 in 250. The resulting secondary PCR product was separated on 1.8% agarose gel, purified, and sequenced directly.

The RACE procedure yielded a PCR product that contained a significant stretch of overlap (200 bp) with the known sequence of the ORF, showing that the RACE-derived sequence was from the clone of interest. Nucleotide sequences obtained from the initial RACE procedure were used to design a second set of nested primers 5' to the first set, and the RACE procedure was repeated. In all, 225 additional bp of the ORF were obtained in this way. A potential initiator codon subsequence (AACATGG) (SEQ ID NO:8) was present at the far 5' region of the RACE-derived sequence. It conformed to the consensus sequence for initiator codons (see Kozak M., *Cell*, 44:283–292, 1886), and further, there was a GC-rich region compatible with a hairpin loop at 14 nucleotides downstream, another feature associated with initiator codons (Kozak M., *Proc. Natl. Acad. Sci. U.S.A.*, 87:8301–8305, 1990).

The RACE procedure was also used with the fetal liver library, by priming with the λgt11 forward primer and custom nested primers based on 5' coding region sequences obtained from the leukocyte library. This provided 118 bp of 5' UT nucleotide sequence, along with a region of overlap with the 5' coding region. The 5' UT nucleotide sequence contained multiple stop codons in all three frames, confirming the location of the initiator codon.

FIG. 1 shows the sequencing strategy used to obtain the nucleotide sequence of the 942 bp ORF. FIG. 2 shows the nucleotide sequence and deduced amino acid sequence of the composite cDNA.

EXAMPLE 2

SEQUENCE ANALYSIS OF PINCH POLYPEPTIDE AND POLYNUCLEOTIDE

Nucleic acid subsequences and ORFs were examined by the MacVector sequence analysis software (IBI). Translated protein subsequences and measures of hydrophilicity (see Kyte J. and Doolittle, R. F., *J. Mol. Biol.* 157:105–132, 1982), surface probability (see Emini, et al., *J. Virol.* 55:836–839, 1985), flexibility (see Karplus P. A. and Schulz, G. E., *Naturwiss.* 72:212–213, 1985), and antigenic index (Jameson B. A. and Wolf, H., *Comput. Applic. Biosciences* 4:181–186, 1988) were obtained from MacVector as well. Nucleic acid sequences and translated protein sequences were aligned to the available databases via the BLAST algorithm (see Altschul, et al., *J. Mol. Biol.* 215:403–410, 1990). Database comparisons were performed at the National Center for Biotechnology Information using the BLAST network service. Databases used included Gen-Bank, EMBL, SWISS-PROT, and Brookhaven Protein Data Bank. Alignment of the cDNA ORF to the available databases using the BLAST algorithm showed homology to the LIM family of proteins. The new LIM protein reported here is unique in the LIM family because it has five LIM domains, as shown in Table 1, rather than one to three domains. It is also notable in that there is a modification of the LIM motif in this protein. Instead of a $C_2HC$ type first finger of each finger doublet, $C_2H_2$ type fingers are substituted in the third and fourth LIM domains, and a $C_4$ type finger is substituted in the fifth LIM domain. The modified LIM domain motif is: $CX_2CX_{16-19}C/HX_2C/HX_2CX_2CX_{16-21}CX_{1-3}C/H/D$(SEQ ID NO:17). This new protein has been named PINCH, (for particularly interesting new Cys-His protein), to suggest its probable function as a binding protein via its zinc fingers.

Analysis of the protein structure of PINCH indicated that the PINCH cDNA ORF encodes a 314 amino acid polypeptide with a calculated molecular mass of 35,799 kDa. It contains 33 cysteines (10% of the total number of amino acids) and 16 histidines (5%). The estimated pI is 8.47. Analysis of the first 100 and remaining 214 residues separately showed that the first 100 residues have a pI of 5.37 and are enriched in phenylalanine (10%) and glutamic acid (10%), while the remaining 214 residues have a pI of 9.23, and are enriched in lysine (9%). A potential N-glycosylation site is present at residue 87 from the amino terminus. Three cytochrome c heme binding motifs are present beginning at residues 118, 135, and 181 in the second and third LIM domains, and a potential zinc finger of the $C_4$ type is present beginning at residue 181, encompassing the linker between the second and third LIM domains. Analysis of hydrophilicity, surface probability, flexibility and antigenic index are shown in FIG. 3. There is no hydrophobic region of sufficient length to suggest the presence of a membrane-spanning domain. There are multiple surface-exposed regions, including a number with predicted high antigenicity.

TABLE 1

THE FIVE PINCH LIM DOMAINS

| Domain | Residues | CX2C | X16–19 | C/HX2C/H |
|---|---|---|---|---|
| First  | 10–62   | CERC | KGGFAPAEKIVNSNGELY | HEQC |
| Second | 71–121  | CHQC | GEEFIIGRVIKAMNNSW  | HPEC |
| Third  | 135–184 | CQKC | HAIIDEQPLIFKNDPY   | HPDH |
| Fourth | 193–243 | CGAC | RRPIEGRVVNAMGKQW   | HVEH |
| Fifth  | 252–303 | CFHC | NRVIEGDVVSALNKAW   | CVNC |

| X2 | CX2C | X16–21 | CX1–3C/H/D | LINKER |
|---|---|---|---|---|
| FV | CAQC | FQQFPEGLFYEFEGRKY | CEHD | FQMLFAPC (SEQ ID NO: 9) |
| FR | CDLC | QEVLADIGFVKNAGRHL | CRPC | HNREKARGLGKYI (SEQ ID NO: 10) |
| FN | CANC | GKELTADARELKGELY  | CLPC | HDKMGVPI (SEQ ID NO: 11) |
| FV | CAKC | EKPFLGHRHYERKGLAY | CETH | YNQLFGDV (SEQ ID NO: 12) |
| FA | CSTC | NTKLTLKNKFVEFDMKPV | CKKC | YEISIGAEEKT (SEQ ID NO: 13) |

PINCH is unique among LIM proteins in that it has all three possible terminal zinc-coordinating residues in the second finger of its LIM domains (three cysteine, one histidine, and one aspartate). Four proline residues occur in the zinc-coordinating finger bases (CX2C, etc.) of the second and third LIM domains, and both domains end with cysteine, the least frequent of the terminal zinc-coordinating residues in the LIM proteins reported to date. Analysis of 20 LIM domain proteins was undertaken to determine the correlation of the occurrence of proline in the finger base with a terminal cysteine in the second finger. Seven proteins with LIM domains ending in cysteine (rat and mouse CRIP, rat ESP1, human CRP, chicken CRP, rat CRP, chicken zyxin, and PINCH) contain proline residues in the finger bases, whereas twelve LIM proteins with terminal histidine or aspartate residues (nematode lin-11, rat isl-1, salmon isl-1, nematode mec-3, rat LH-2, fruitfly apterous, human and mouse rhombotin 1 and rhombotin 2, frog Xlim-1, sunflower pollen specific protein, rat rit-18, and golden hamster Imx-1) have no proline in the finger bases. Japanese quail CRP has two LIM domains ending in cysteine, but no proline in its finger bases. Table 2 shows that there is a statistically significant association of the presence of proline in the zinc-coordinating finger bases with the presence of cysteine as the terminal residue in the second finger of the LIM domain.

TABLE 2

| Terminal residue | Finger base | | |
|---|---|---|---|
|  | Proline Residues | Other residues | Total residues |
| Cysteine | 20 | 154 | 174 |
| Histidine or aspartate | 0 | 238 | 238 |
| Total | 20 | 392 | 412 |

20 LIM domain proteins examined, Chi-square = 28.752, p < 0.001, Fisher's exact test = p < 0.001
The presence of proline in the zinc-coordinating finger bases is strongly associated with the presence of cysteine instead of histidine or aspartate as the terminal residue of the LIM domain*.

Many LIM domain proteins in the proline-free, terminal histidine or aspartate group are nuclear proteins, and most are believed to be transcription factors. In contrast, most proteins in the proline-containing, terminal cysteine group are cytoplasmic, and function in protein-protein interactions, such as zyxin and CRP. The presence of proline in the finger base may result in a different finger configuration, and/or differences in metal coordination that may correlate with function.

PINCH translated amino acid sequence was compared with that of AE1 using the MacVector protein analysis software. The comparison revealed that PINCH residues 149–157 are homologous to both AE1 autoepitopes (Table 3). The PINCH autoepitope, FKNDPYHPD (SEQ ID NO:3), is located in the first finger of the third LIM domain from the amino terminus, and is predicted to be surface-exposed and to have high antigenicity (FIG. 4). Homology of a continuous PINCH amino acid sequence to two discontinuous AE1 amino acid sequences was surprising, because the two AE1 autoepitopes are not homologous. However, as shown by the consensus sequence in Table 3, the first three amino acids in the PINCH autoepitope, FKN, are identical to the first amino acid of the AE1 593–601 autoepitope and the two preceding amino acids, and the last four amino acids in the PINCH autoepitope, YHPD, are identical to the last amino acid in the AE1 813–818 autoepitope and the following three amino acids. This overlap may explain the synergy noted in the activity of the peptides corresponding to AE1 593–601 and AE1 813–818 in inhibition of binding of IgG autoantibody to aged RBCs.

TABLE 3

| Residues | Amino acids* | SEQ ID |
| --- | --- | --- |
| AE1 591–2601[a] | FK<u>NSSYFPGKL</u> | NO: 14 |
| AE1 813–823[a] | F<u>KPPKYHPD</u>VP | NO: 15 |
| PINCH 149–159 | <u>FKNDPYHPD</u>HF | NO: 3 |
| Consensus | FKN-YHPD | |

*epitopes underlined (AE1 593–601, AE1 813–818, PINCH 149–157)
[a](Kay, et al., Proc. Natl. Acad. Sci., U.S.A., 87:5734, 1990)

There are a number of unusual features in the region of PINCH that contains the autoepitope, including modification of the LIM motif, the potential zinc finger of the $C_4$ type in the linker, three cytochrome c heme binding motifs, and four proline residues in the zinc-coordinating finger bases. The location of the autoepitope and surrounding features are indicated in FIG. 4. Although not wanting to be bound by any particular theory, it is believed that this figure has two models for the structure of PINCH. Model A shows ten zinc fingers, each LIM domain consisting of a double finger. The PINCH autoepitope is contained in the first finger of the third LIM domain. Model B shows nine zinc fingers, with the second finger of the second LIM domain and the first finger of the third LIM domain replaced by a single finger. This single finger is shorter than the two fingers it replaces. The PINCH autoepitope is contained in the linker following the short finger, rather than in the finger itself. It is possible that PINCH may assume either configuration (or intermediate configurations) under varying conditions, such as changes in redox potential or metal concentration, or autoantibody binding.

EXAMPLE 3

NORTHERN AND SOUTHERN ANALYSIS

Three Northern blots containing poly-A RNA from a variety of human tissues and a Southern blot containing EcoRI-restricted genomic DNA from a number of species were obtained from Clontech Laboratories. A 1 kb PCR product corresponding to PINCH cDNA (3' to the EcoRI site) and a b-actin probe provided by Clontech were radiolabeled with [a-$^{32}$P]dCTP by random priming (Mixed Primer Labeling System II, Clontech), and purified (CHROMA SPIN-100 columns, Clontech). Probes were added at $1\times10^6$ cpm/ml of fresh hybridization solution.

Northern blots were prehybridized for 3 hours at 42#C, and hybridized overnight at 42#C. The hybridization buffer contained 5× SSPE, 10× Denhardt's solution, 100 ug/ml salmon sperm DNA, 50% formamide, and 2% SDS. Blots were washed three times for 10 minutes in a solution of 2× SSC, 0.05% SDS at room temperature, and twice for 20 minutes in a solution of 0.1× SSC, 0.1% SDS at 50#C. The Southern blot was prehybridized for 3 hours at 65#C, and hybridized overnight at 65#C. The hybridization buffer was the same as for the Northern blots, with the omission of formamide. The Southern blot was washed three times for 10 minutes in a solution of 2× SSC, 0.05% SDS at room temperature, and twice for 20 minutes in the same wash solution at 60#C.

Blots were exposed to Xray film with two intensifying screens at −70#C for times varying from 6 hours to 1 week.

Figure 5A:
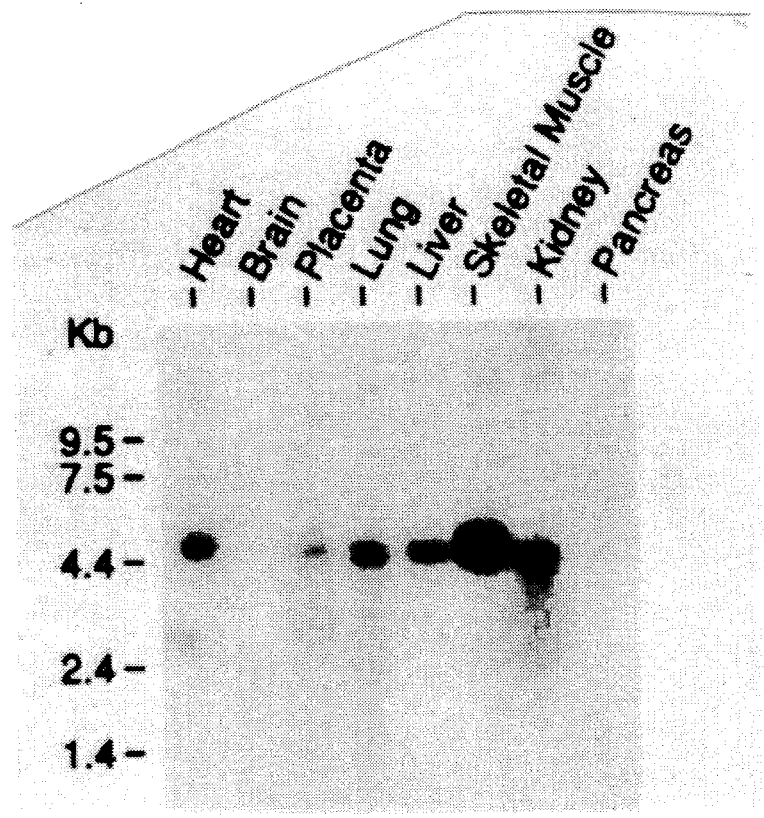
FIG. 5 shows Northern blot analysis of PINCH expression in human tissues.
Figure 5B:
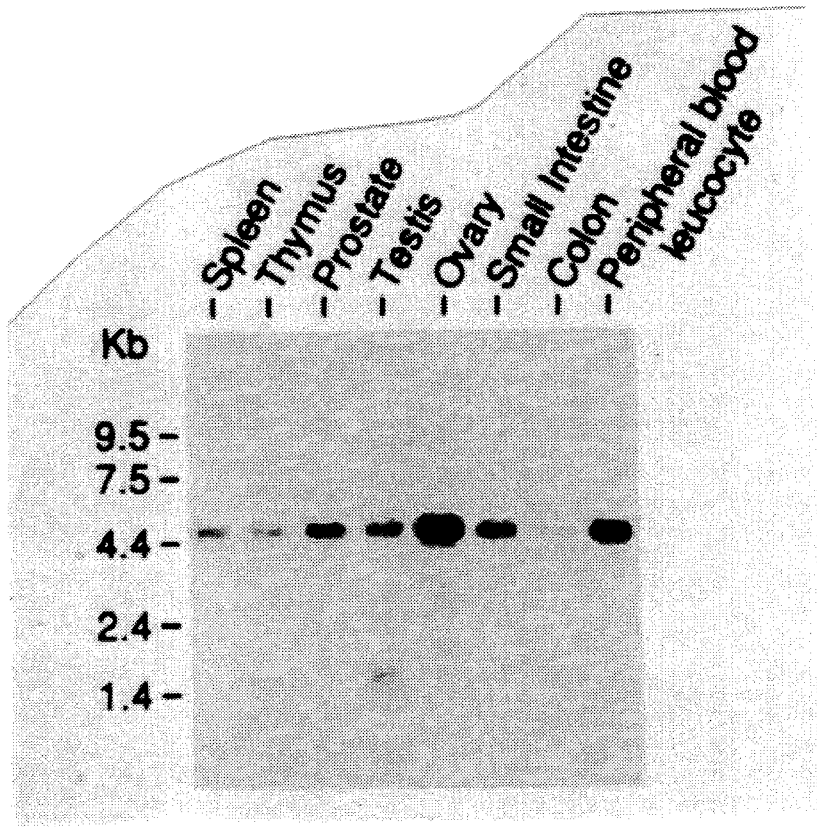

The Northern blots containing poly-A mRNA from various human tissues were probed (FIG. 5). Poly-A RNA on nylon membranes was probed with a radiolabeled PCR product corresponding to cPINCH #1, which contains the ORF 3' to the EcoRI site. Blots A and B were exposed for 3 days, and showed PINCH expression in all tissues tested except brain. Blot C, containing poly-A RNA from various brain tissues, showed no PINCH expression after exposure for 3 days but expression was detected after exposure for 1 week. The apparent size of the PINCH mRNA in blots A and B is 4.6 kb. The apparent size of the mRNA detected in blot C is smaller. However, when blot C was reprobed with the b actin probe, the mRNA detected was also smaller than expected. Hybridization with a b-actin probe showed that all lanes contained mRNA. In conclusion, a 4.6 kb mRNA which hybridized with a PINCH-specific PCR product showed in 15 tissues examined, but no hybridization occurred to mRNA from brain tissue (FIG. 5A and 5B). A second, smaller mRNA (1.6 kb) was detected in testis.

Figure 5C:
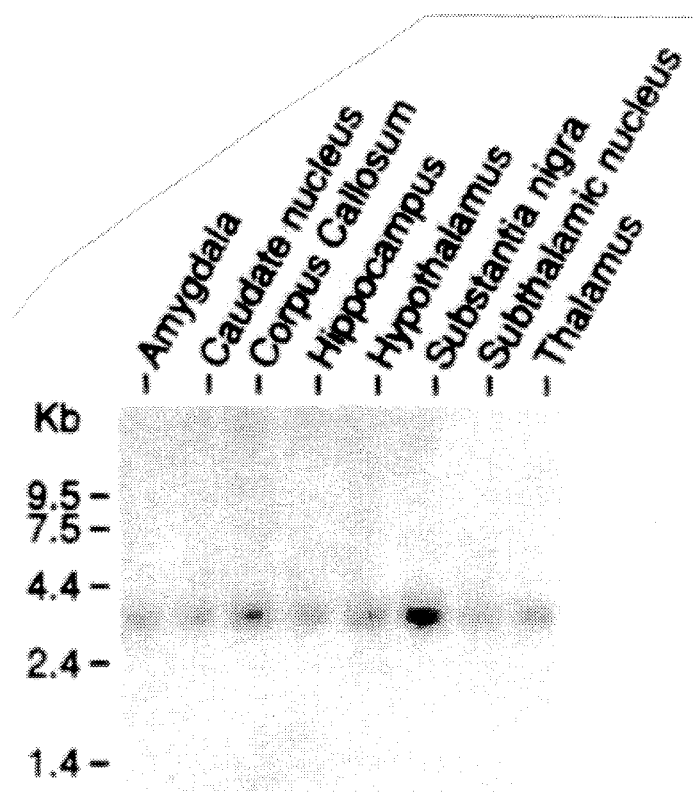

To confirm lack of PINCH expression in brain, a Northern blot containing poly-A mRNA from eight different parts of the brain was probed (FIG. 5C). No PINCH mRNA was evident on this blot with exposure times similar to those used for blots A and B in FIG. 5. However, message was detected in all brain tissues after one week exposure time, indicating that brain has very low expression of PINCH, or that the brain tissue samples contained a minor component of non-neural tissue.

Figure 6:
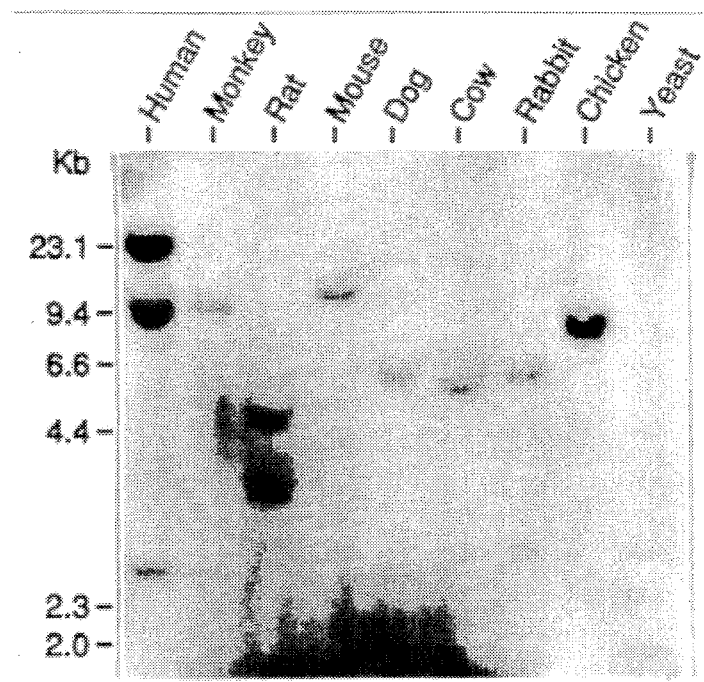
FIG. 6 shows conservation of the PINCH gene in vertebrates by Southern blot analysis (3 day exposure). Size markers in kb are on the left.

FIG. 6 shows Southern blot analysis indicating that PINCH is highly conserved among vertebrates (3 day exposure). EcoRI-restricted genomic DNA on a nylon blot was hybridized with a radiolabeled PCR product corresponding to cPINCH #1, which contains the ORF 3' to the EcoRI site. Size markers in kb are on the left. The PINCH-specific PCR product showed strong hybridization to EcoR1-restricted genomic DNA from human, monkey, rat, mouse dog, cow, rabbit, chicken, but not yeast.

The foregoing is meant to illustrate, but not to limit, the scope of the invention. Indeed, those of ordinary skill in the art can readily envision and produce further embodiments, based on the teachings herein, without undue experimentation.

I claim:

1. An isolated PINCH protein consisting of the amino acid of SEQ ID NO:2.

2. A synthetic peptide consisting of the amino acid sequence of SEQ ID NO:3.

* * * * *